(12) United States Patent
Buscemi et al.

(10) Patent No.: US 6,299,597 B1
(45) Date of Patent: *Oct. 9, 2001

(54) PERCUTANEOUS REPAIR OF CARDIOVASCULAR ANOMALIES AND REPAIR COMPOSITIONS

(75) Inventors: Paul J. Buscemi, Long Lake; Fertac Bilge, Arden Hills; Thomas J. Holman, Minneapolis, all of MN (US)

(73) Assignee: SciMed Life Systems, Inc., Maple Grove, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/978,190

(22) Filed: Nov. 25, 1997

Related U.S. Application Data

(63) Continuation of application No. 08/532,257, filed on Sep. 22, 1995, now abandoned, which is a continuation of application No. 08/122,918, filed on Sep. 16, 1993, now abandoned.

(51) Int. Cl.[7] ................................................ A61M 29/00
(52) U.S. Cl. .............................. 604/101.03; 604/101.05
(58) Field of Search ........................... 604/96.01, 101.03, 604/101.05

(56) References Cited

U.S. PATENT DOCUMENTS

| | | |
|---|---|---|
| 3,173,418 | 3/1965 | Baran . |
| 3,657,744 | 4/1972 | Ersek . |
| 3,868,956 | 3/1975 | Alfidi et al. . |
| 3,991,767 | 11/1976 | Miller, Jr. et al. . |
| 4,140,126 | 2/1979 | Choudhury . |
| 4,329,993 | 5/1982 | Lieber et al. . |

(List continued on next page.)

FOREIGN PATENT DOCUMENTS

| | | |
|---|---|---|
| 0 221 570 | 5/1987 | (EP) . |
| 0 335 341 | 10/1989 | (EP) . |
| 0 508 473 | 10/1992 | (EP) . |
| 0 539 237 | 4/1993 | (EP) . |
| 0 556 850 | 8/1993 | (EP) . |
| 94/21320 | 9/1994 | (WO) . |

OTHER PUBLICATIONS

Improved Dilatation Catheter Balloons, by Stanley B. Levy, Ph.D., *Journal of Clinical Engineering*, vol. 11, No. 4, Jul.–Aug., 1986, pp. 291–296.

"Intracvascular Stenting for Stenosis of Aortocoronary Venous Bypass Grafts", Urban et al., *JACC*, vol. 13, No. 5, Apr. 1989, pp. 1085–1091.

(List continued on next page.)

*Primary Examiner*—Anthuan T. Nguyen
*Assistant Examiner*—Jeremy Thissell
(74) *Attorney, Agent, or Firm*—Vidas, Arrett & Steinkraus, P.A.

(57) ABSTRACT

Percutaneous repair of cardiovascular anomalies via the introduction of a photoactivated biopolymer introduced to the affected site via a catheter system.

1 Claim, 5 Drawing Sheets

U.S. PATENT DOCUMENTS

| | | | |
|---|---|---|---|
| 4,423,725 | | 1/1984 | Baran et al. . |
| 4,445,892 | * | 5/1984 | Hussein et al. ............... 604/101 |
| 4,503,569 | | 3/1985 | Dotter . |
| 4,512,338 | | 4/1985 | Balko et al. . |
| 4,553,545 | | 11/1985 | Maass et al. . |
| 4,617,932 | | 10/1986 | Kornberg . |
| 4,624,847 | | 11/1986 | Ayer et al. . |
| 4,636,195 | | 1/1987 | Wolinsky . |
| 4,638,803 | | 1/1987 | Rand . |
| 4,733,665 | | 3/1988 | Palmaz . |
| 4,739,762 | | 4/1988 | Palmaz . |
| 4,740,207 | | 4/1988 | Kreamer . |
| 4,787,899 | | 11/1988 | Lazarus . |
| 4,820,298 | | 4/1989 | Leeven et al. . |
| 4,872,874 | | 10/1989 | Taheri . |
| 4,875,480 | | 10/1989 | Imbert . |
| 4,878,906 | | 11/1989 | Lindemann et al. . |
| 4,911,713 | | 3/1990 | Sauvage et al. . |
| 4,923,464 | | 5/1990 | DiPisa, Jr. . |
| 4,969,890 | | 11/1990 | Sugita et al. . |
| 4,983,166 | | 1/1991 | Yamawaki . |
| 4,994,003 | | 2/1991 | Shockey et al. . |
| 4,994,033 | * | 2/1991 | Shockey et al. ............... 604/101 |
| 5,034,001 | | 7/1991 | Garrison et al. . |
| 5,041,090 | | 8/1991 | Scheglov et al. . |
| 5,049,132 | | 9/1991 | Shaffer et al. . |
| 5,053,033 | | 10/1991 | Clarke . |
| 5,059,211 | | 10/1991 | Stack et al. . |
| 5,078,736 | | 1/1992 | Behl . |
| 5,087,244 | | 2/1992 | Wolinsky et al. . |
| 5,092,841 | | 3/1992 | Spears . |
| 5,100,429 | * | 3/1992 | Sinofsky ........................ 606/195 |
| 5,104,399 | | 4/1992 | Lazarus . |
| 5,108,407 | | 4/1992 | Geremia et al. . |
| 5,122,154 | | 6/1992 | Rhodes . |
| 5,151,105 | | 9/1992 | Kwan-Gett . |
| 5,213,517 | * | 5/1993 | Kratzer ........................... 604/101 |
| 5,213,580 | * | 5/1993 | Slepian et al. .................. 623/1 |
| 5,219,335 | | 6/1993 | Willard et al. . |
| 5,232,444 | | 8/1993 | Just et al. . |
| 5,256,141 | * | 10/1993 | Gencheff et al. ............... 604/101 |
| 5,261,875 | * | 11/1993 | Spears ............................. 604/280 |
| 5,284,868 | * | 2/1994 | Dell et al. ...................... 514/454 |
| 5,286,254 | * | 2/1994 | Shapland et al. .............. 604/21 |
| 5,314,409 | * | 5/1994 | Sarosiek et al. ............... 604/101 |
| 5,318,531 | * | 6/1994 | Leone ............................. 604/101 |
| 5,328,471 | * | 7/1994 | Slepian ........................... 604/101 |
| 5,336,178 | * | 8/1994 | Kaplan et al. ................. 604/53 |
| 5,344,419 | | 9/1994 | Spears . |
| 5,344,444 | | 9/1994 | Glastra . |
| 5,405,322 | * | 4/1995 | Lennox et al. ................. 604/53 |
| 5,611,775 | * | 3/1997 | Machold et al. ............... 604/53 |
| 5,871,449 | * | 2/1999 | Brown . |
| 5,902,268 | * | 5/1999 | Saab . |
| 5,941,893 | * | 8/1999 | Saadat . |

OTHER PUBLICATIONS

"Results of Intracoronary Stents for Management of Coronary Dissection After Balloon Angioplasty", Haude, et al., *The American Journal of Cardiology* Apr. 1, 1991, vol. 67, pp. 691–696.

"Transfemoral Intraluminal Graft Implantation for Abdominal Aortic Aneurysms", Parodi, et al., *Annals of Vascular Surgery*, vol. 5, No. 6–1991, pp. 491–499.

"A View of Vascular Stents" Schatz, *Circulation*, vol. 79, No. 2, Feb. 1989, pp. 445–457.

"Transfemoral Endovascular Aortic Graft Placement", Chuter, et al., *Journal of Vascular Surgery*, Aug. 1993, vol. 18, No. 2, pp. 185–197.

"Percutaneous Transfemoral Insertion of a stented Graft to Repair a Traumatic Femoral Arteriovenous Fistula", Marin, et al., *Journal of Vascular Surgery*, Aug. 1993, vol. 18, No. 2, pp. 299–302.

* cited by examiner

PERCUTANEOUS REPAIR OF CARDIOVASCULAR ANOMALIES AND REPAIR COMPOSITIONS

This application is a continuation of application Ser. No. 08/532,257, filed Sep. 27, 1995, now abandoned, which is a continuation of application Ser. No. 08/122,918 filed on Sep. 16, 1993, now abandoned.

BACKGROUND OF THE INVENTION

The incidence of vascular aneurysms is increasing due to improved longevity of the population as well as improvements in the methods of diagnosing for these afflictions. Hertzer recently reported in *Vascular Surgery* that approximately 3% of the general population may be afflicted with aortic aneurysms. Further, specific incidence of aortic aneurysm correlates to a great degree with related risk factors. For instance, approximately 53% of all patients demonstrating femoral or popliteal aneurysms also were indicated to have aortic aneurysms. The prevalence of aneurysms increase rapidly after 55 years of age. Akkerselijk et al reported a AAA rate of 11.4% in men over 60.

Health care costs for the repair of aneurysms and dissections of the aorta, iliac, femoral and popliteal arteries is presently assumed to be in the vicinity of 150–200 million dollars annually and is rising at a significant level due to greater ability to diagnose and treat these afflictions, as well as because of the aging of the general population.

The repair of aneurysms and dissections found in the cardiovascular tree has to a great degree reflected the numerous advancements occurring in the fields of surgery, anesthetics and bio-devices. Since the 1950's successful repair of aneurysms has been possible through surgical treatment and to the present day standard treatment for aneurysms, dissection and septal defects includes surgical intervention typically resulting in the implant of a prosthesis to replace the dissected diseased tissue or span the gap of a septal defect. There are several prosthetic devices available for the repair of these anomalies. However, in spite of the relatively high degree of success being indicated by the surgical repair of vascular aneurysms (actuarial rates for the repair of aortic aneurysms indicate less than 3% morbidity being associated with this procedure) there exists numerous reasons for improvement of the processes used. For example, there is the need to further minimize trauma to the patients. There is also the need to minimize hospitalization time. There is a need to minimize expense associated with the repair procedure.

SUMMARY OF THE INVENTION

The present invention is directed towards the use of fluid polymer compositions for vascular repair and an accompanying catheter system which is applicable to the percutaneous repair of vascular aneurysms, dissections and the like.

Specifically, this invention relates to vascular diseases and anomalies such as aneurysms, dissections, lesions and septal defects in which the afflicted area is not surgically excised and replaced but rather is repaired by the localized delivery of a fluid polymerizable or crosslinkable material to the diseased site and the following stabilization of the polymer by photo-activation, heat activation or chemical means of this material in situ, resulting in a solid repair material at the site. The pre-polymer is delivered to the site by accessing the vasculature via the percutaneous introduction of a catheter (specifically designed for this application) into a vessel such as the femoral, brachial or carotid artery. Following delivery to the afflicted area, the fluid polymer may be molded via the use of the catheter. The pre-polymer is stabilized i.e. solidified in situ either by polymerization or crosslinking via the introduction of light or heat energy, chemicals, or chemical initiators. A relatively smooth transition between the polymer network and the natural vessel may be achieved either by shaping the proximal and distal portion of the implant generated or by controlling the physical and material properties of the polymer. Lastly, the catheter system is removed thus leaving behind a crosslinked polymeric network affecting the repair of the diseased site.

DETAILED DESCRIPTION

The present invention is directed towards catheter systems and polymeric materials which are applicable to the percutaneous repair of or creation of lumens or conduits in saphenous vein grafts (SVG), vascular aneurysms, septal defects, renal and urinary ducts and conduits, dissections and the like. Specifically there is disclosed a method of treatment for vascular diseases and anomalies, such as SVGs following angioplasty, aneurysms, dissections, lesions and septal defects in which the afflicted area is not surgically excised and replaced but rather is repaired by localized delivery of crosslinkable polymeric material delivered directly to the diseased site and the subsequent stabilization, as by chemical heat or photoactivated crosslinking in situ. The crosslinkable polymer is delivered to the site in a flowable form by accessing the vasculature via the percutaneous introduction of a catheter (specifically designed for this application) into a vessel such as the aorta, femoral, or coronary arteries. Following delivery to the afflicted area, the polymer may be molded via the use of a balloon on the catheter. The polymer is crosslinked or polymerized in position via the introduction of light energy, heat, or chemical means which will bond and form a stable polymeric network. Lastly, the catheter system is removed, leaving behind a crosslinked polymeric network with a lumen, thus effecting the repair of the diseased site.

Figure 1:
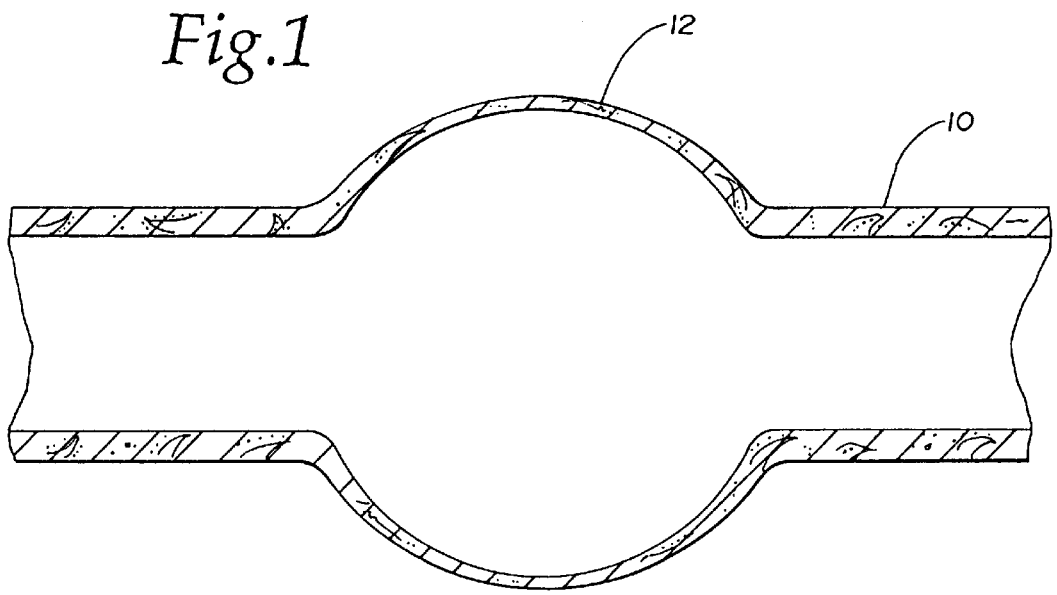
FIG. 1 shows a diagrammatic representation of an aneurysm. The diameter of an aneurysmal site can frequently exceed that noted in the healthy tissue to a significant degree.

Referring now to the drawings, FIG. 1 shows a vessel 10 having an aneurysm 12 which has swelled to a diameter larger than the normal size of the vessel. Repair is needed to strengthen the vessel in the area of aneurysm 12.

Figure 2:
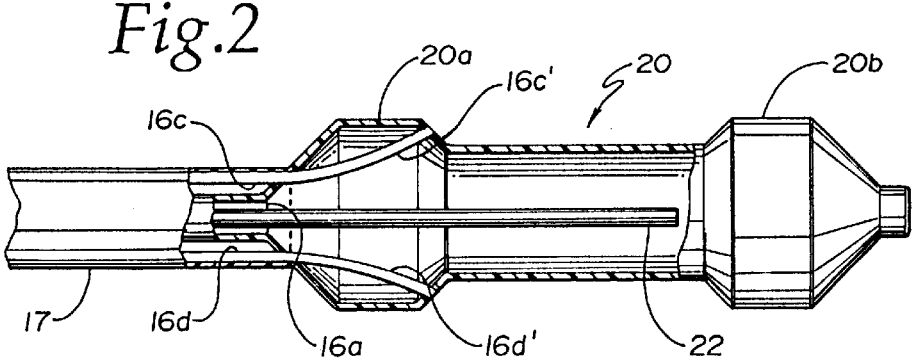
FIG. 2 diagrammatically indicates the distal portion components of a balloon catheter which is applicable to the repair of vascular anomalies such as aneurysms according to this invention. The catheter serves to deliver a repair polymer to the diseased site.
Figure 10:
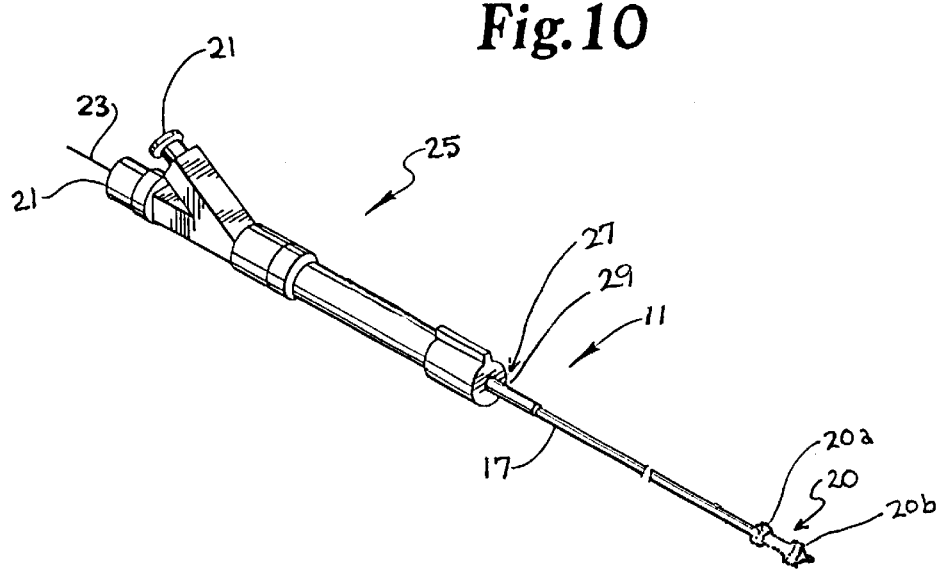
FIG. 10 is a perspective view of a balloon catheter which is applicable to the repair of vascular anomalies such as aneurysms according to this invention.

A catheter system specifically constructed and arranged to effect the needed repair is shown in FIGS. 2 and 10. The catheter shown generally at 11 in FIG. 10, includes multi-lumenal tubing 17 consisting of several lumens with access ports, indicated generally at 27 in FIG. 10, located in the catheter hub portion, as shown at 29 in FIG. 10. The key components of the catheter system are: multilumenal tubing 17 consisting of minimally three fluid ports. The tubing may be constructed from any biologically acceptable material examples of which would include the polyolefins, urethane and polyester type materials. A balloon generally designated 20, having enlarged end portions 20a (proximal) and 20b (distal) when partially inflated as seen in FIGS. 2 and 10, embodies a fiber optic light source 22 (or a heat source as known in the art) which may replace a guide wire, as shown at 23 in FIG. 10, as needed during the procedure. As can be seen in FIG. 2, the catheter lumen 16a also serves to inflate and deflate the balloon. Catheter lumen 16a also serves to accept a guide wire (not shown) as needed and/or a fiber optic strand 22 or resistive heat source or the like. Catheter lumen 16c series as pre-polymer inlet port and terminates in a relatively small conduit 16c' which extends through proximal balloon portion 20a to provide a flow of pre-polymer into the area located between the enlarged balloon end portions 20a and 20b. Catheter lumen 16d is similarly constructed and arranged at its end in proximal balloon portion 20a to provide a vent conduit 16d'. The proximal end of the catheter construction may in the known manner include a manifold as shown at 25 in FIG. 10, with access ports 21 and the like in the known manner. FIG. 2 diagrammatically demonstrates a design for the delivery of the polymeric material. The catheter has a balloon with enlarged portions (when partially inflated) on both of its ends. These end portions 20a and 20b are designed to stop blood flow in both directions. There are two ports 16c' and 16d' through the proximal portion 20a of the balloon connecting to the central balloon region i.e., the volume between the balloon end portions. One of these ports 16d' is for flushing the area and venting it while the other 16c' port is for material delivery. Upon placement of the balloon assembly at the desired area, the balloon is partially inflated until the blood flow is cut from both directions. The central area is then flushed and cleaned, followed by the delivery of the polymeric material. At this time the balloon can be further inflated to shape the material (see FIG. 5). When photo crosslinking is desired, the optical fiber is placed in lumen 16a to provide the requisite energy. The balloon will be inflated with a liquid that will be transparent to the wavelength of light used and the fiber may be moved inside the balloon to raster the area.

Figure 3:
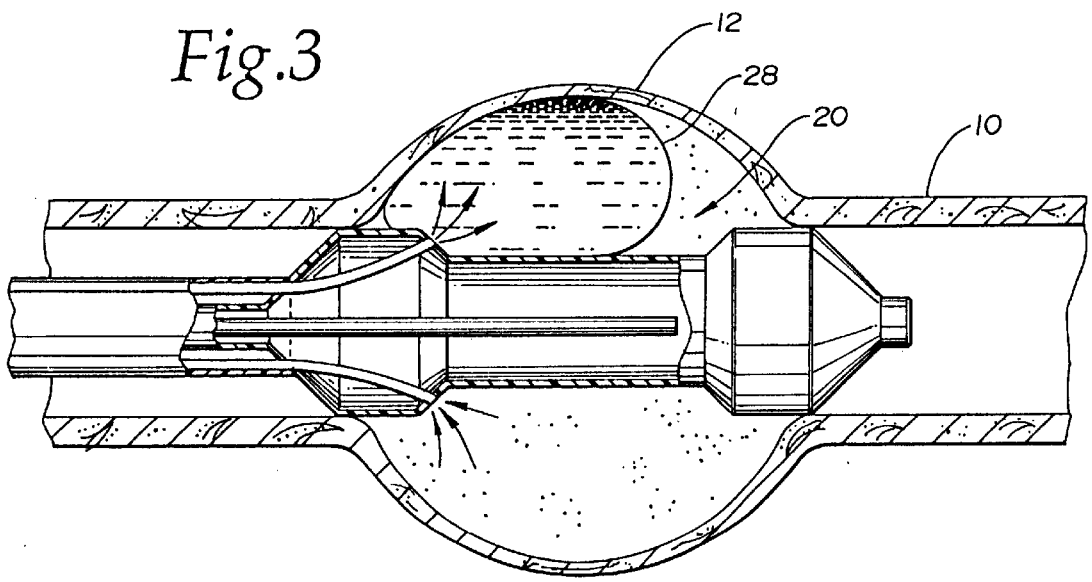
FIG. 3 shows the distal portion of the tissue management catheter of the invention having been introduced to the site of an aneurysm and introducing prepolymer to the site.

In FIG. 3, catheter balloon 20 is shown having been introduced to the aneurysm site 12 for vessel 10 in the known manner. Note that the balloon is introduced to the point at which the balloon when inflated (as shown) seals tight at both sides of the aneurysm to form a sealed area or volume therebetween for enclosing the aneurysm site. Also, the Figure shows that fiber optic light source 22 has been introduced into the balloon at the vicinity of the aneurysm as well as an initial flow of polymeric material 28.

Figure 11:
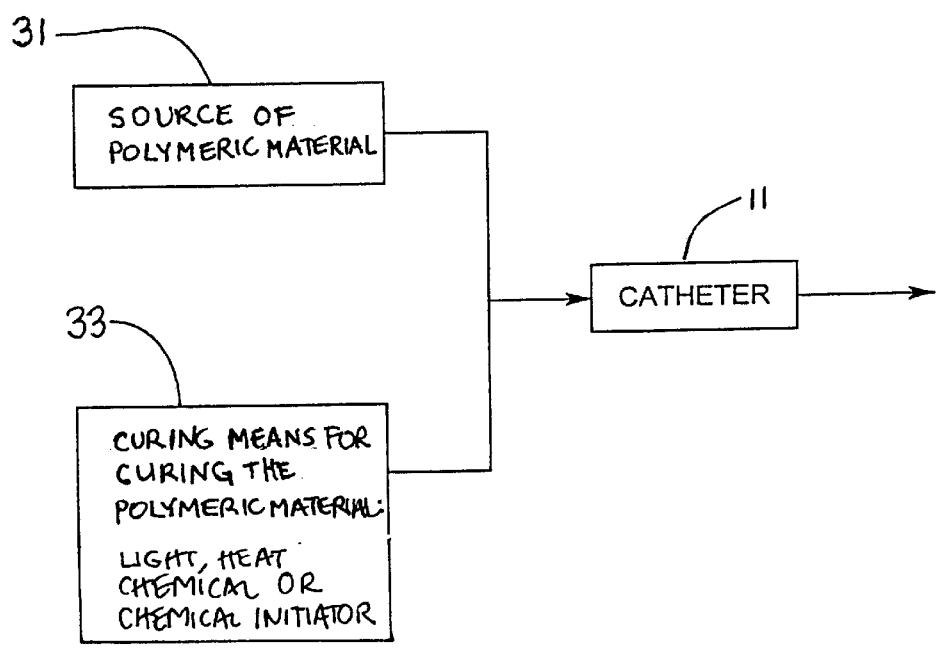
FIG. 11 is a schematic diagram of the catheter of the present invention in combination with a source of polymeric material and a curing means for curing the polymeric material.

FIG. 11 is a schematic diagram of the catheter of the present invention, designated at 11, in combination with a source of polymeric material, designated at 31 and a curing means, designated at 33, for curing the polymeric material 31.

Figure 4:
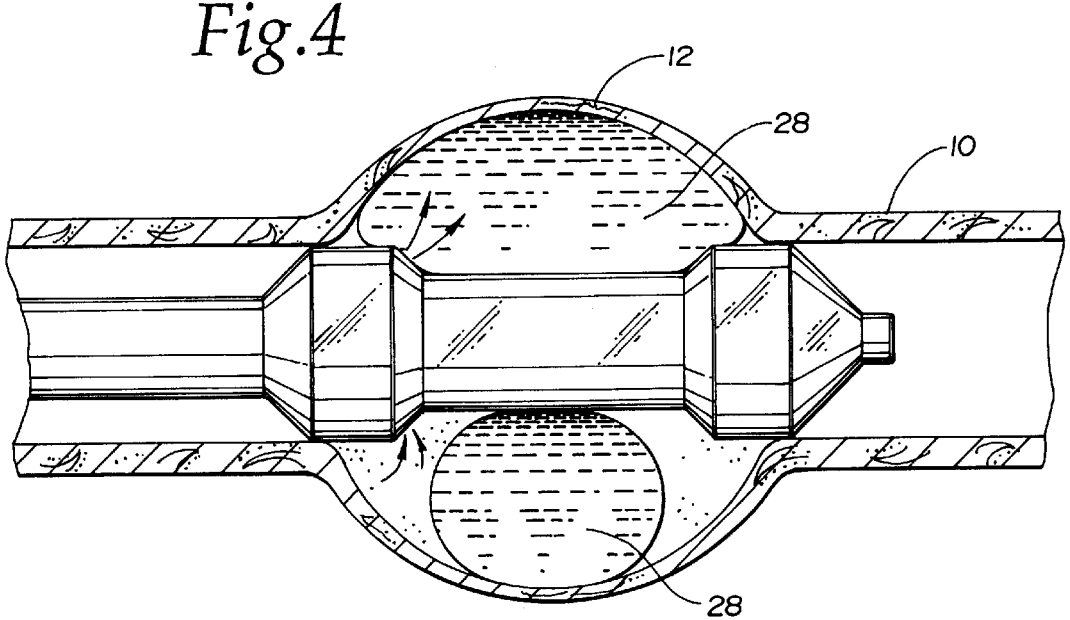
FIG. 4 shows the further introduction of the photoactivatable pre-polymer to the site of an aneurysm. Specifically, the pre-polymer is introduced to the site via the injection of the pre-polymer into the polymer delivery hub of the catheter (not shown).
Figure 5:
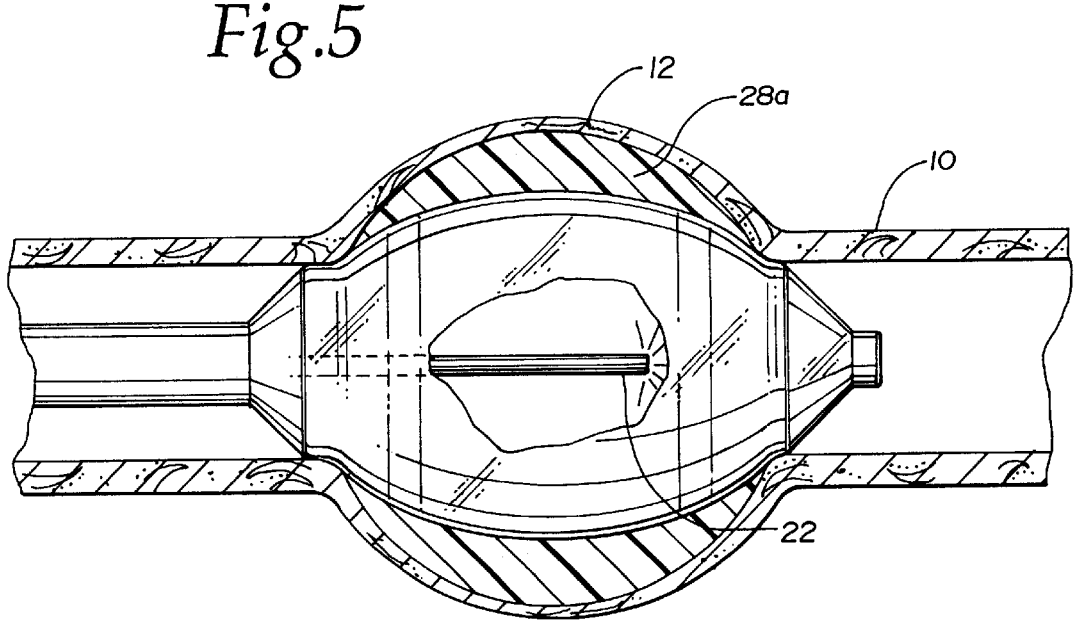
FIG. 5 shows the aneurysmal volume filled with polymer composition and being formed by the expanded balloon of the catheter. At this time the polymer is activated using an energy source such as light; resultantly the pre-polymer becomes crosslinked into position and adds structural stability to the area.
Figure 6:
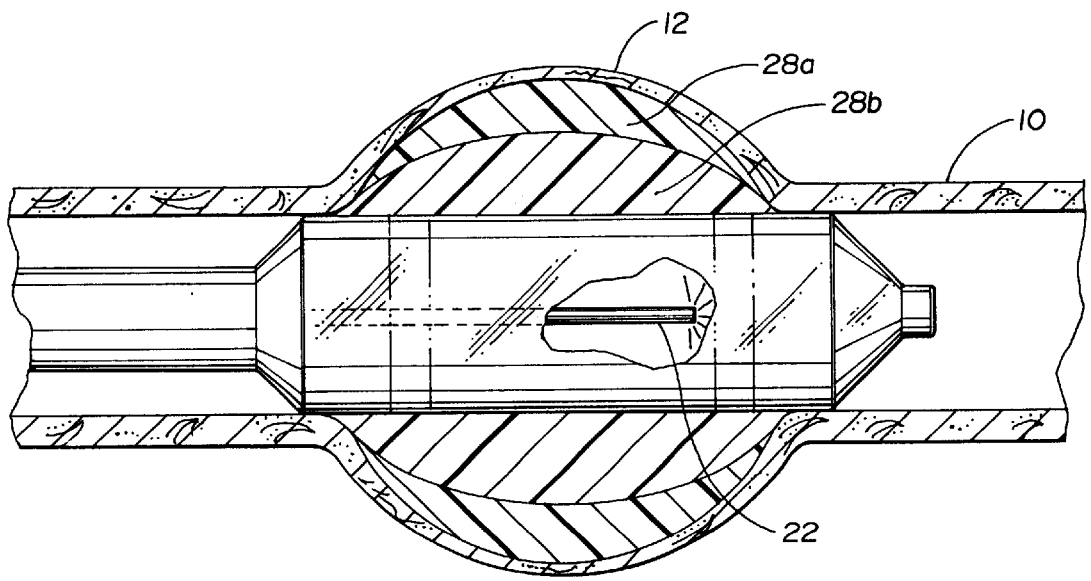
FIG. 6 shows a second layer of pre-polymer being introduced to the site and the resultant fixed body of photoactivated pre-polymer at the aneurysm repair site. As a result the aneurysm has been filled and the internal diameter of this portion has been reduced to match the diameter of the healthy artery with the surrounding healthy portion of the vessel.
Figure 7:
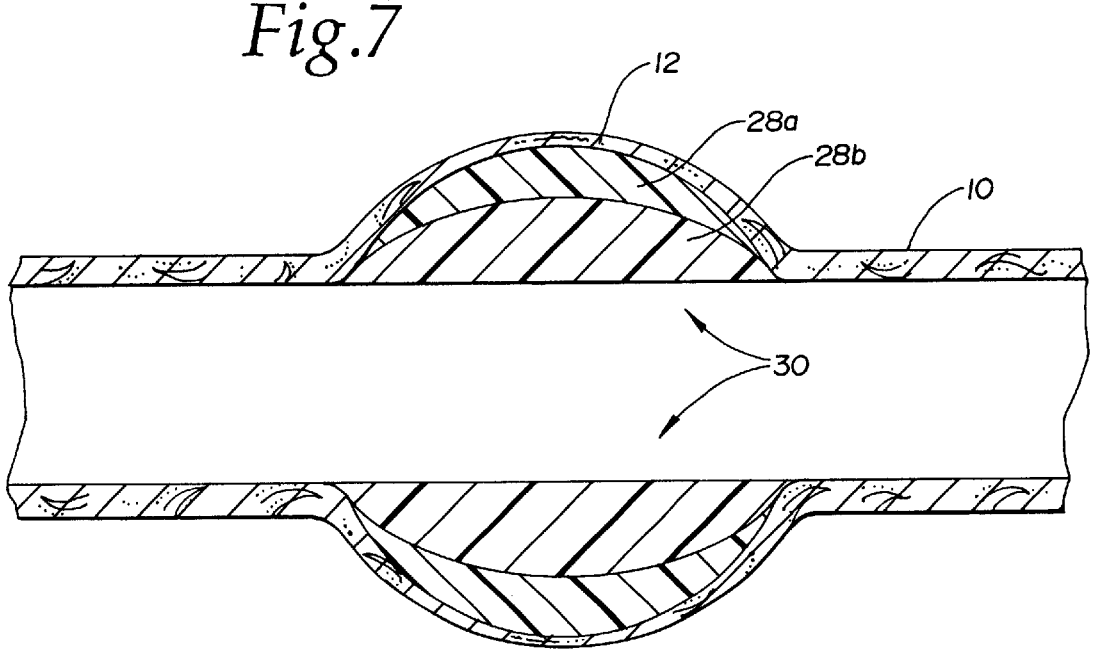
FIG. 7 shows the repaired aneurysm site after the catheter has been withdrawn. Note that the repaired (aneurysmal) portion of the vessel is now isodiametric with the surrounding healthy tissue.

Referring to FIG. 4 it can be seen how the polymer composition 28 is delivered to the site through the lumen 16c' of access port 16c by injection of the fluid composition into the manifold (not shown) or the like at the proximal end of the catheter. The pre-polymer may be injected until partial filling of the aneurysmal volume is effected as shown in FIG. 5. At this time the fiber optic light source 22 is activated using an energy source such as a laser (not shown) to crosslink the pre-polymer. Pre-polymer 28 is more fully described hereinbelow and is crosslinked in situ to such an extent that the fluid character of the polymer composition is lost and it stabilizes into a relatively fixed body 28a as shown in FIG. 5. A second quantity of material 28b may be introduced as shown in FIG. 6 to assure filling of the cavity. It is similarly polymerized or crosslinked in situ. The repaired site 30 is shown in FIG. 7 after withdrawal of the catheter.

The photo or chemically crosslinkable material may be formed into an intraluminal graft or other implantable device. This device which may be soft and easily manipulatable upon introduction and will harden after being placed in its intended position by crosslinlking, polymerization, or the like. In the case of an intraluminal graft, the graft will be delivered percutaneously and when in position will be expanded with the balloon as necessary. The graft will then be crosslinked and secured in position by hardening.

Figure 8:
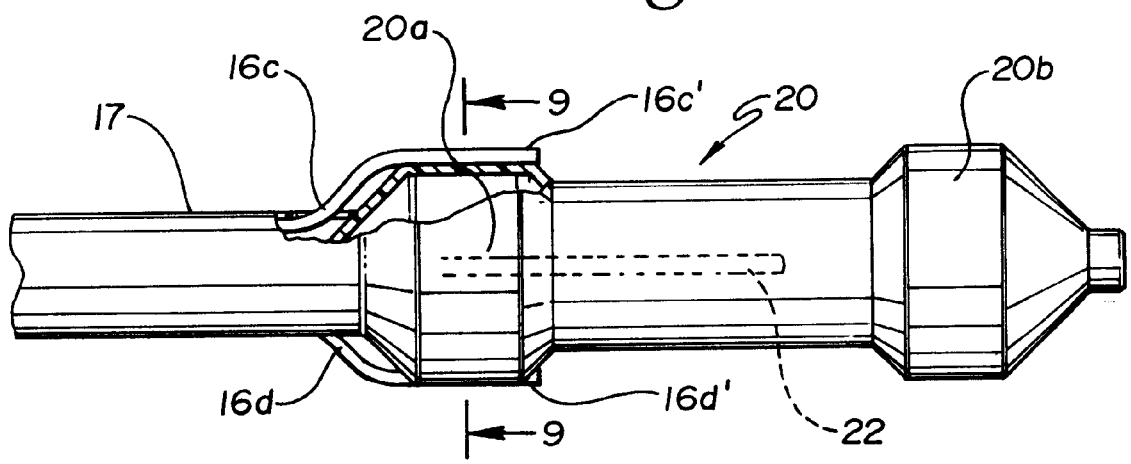
FIG. 8 shows a modified design of the tissue management catheter. In this version the delivery and venting ports are placed on the surface of the proximal end of the balloon.
Figure 9:
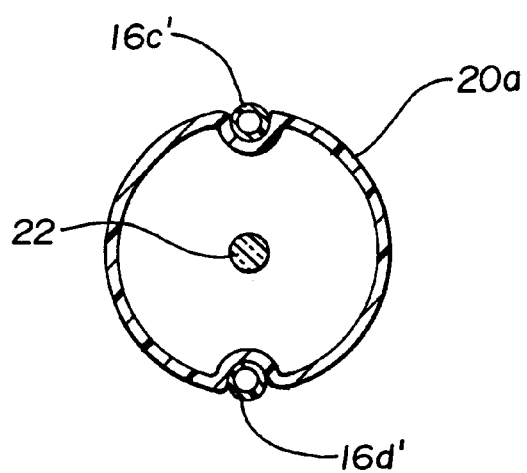
FIG. 9 is a cross-sectional view along 9—9 of FIG. 8.

FIGS. 8 and 9 show a modified catheter system designed for the needed repair similar to the system shown in FIG. 2. In this design the tubes 16c and 16d used for material delivery and venting are placed on the surface of the balloon. Grooves may be formed as shown on the proximal end 20a of the balloon to accommodate these tubes. This may be needed to achieve complete sealing of the vessel by the proximal end of the balloon.

Polymer Compositions

The polymeric compositions function in the broader sense as a protective material and may even include a drug. Also, the material is preferably adhesive-like and capable of changing from a "first state" favorable form of a material (allowing injection through the catheter) to a "second state" solid, semi-solid or paste-like form, which conforms to the interior wall of a blood vessel or other repair site in the presence of blood flow to provide a protective covering and seal over flaps, aneurysms, perforations, cracks, and the like. The "first state" must be fluid-like so that it flows through the catheter lumen and out of the small port in the proximal end portion of the catheter balloon. The "second state" must protect the repair site and remain in place when subjected to blood flow, torsion, and other physical events.

Various kinds of polymeric material will function satisfactorily for the purposes of this invention. A material which polymerizes in situ with heat or UV eg., polylactic acid (PLA) will suffice. Reactant mixtures e.g., polyvinyl acetate and collagen are also acceptable. Two part systems which will foam and crosslink in situ like polymesh pre-polymer are accepted.

The polymeric material to be used for structural support or other purposes may be a photo crosslinkable monomer system. Examples of such a system are photoinitiator and an unsaturated polyester. The unsaturated polyester may be prepared by the methacrylation of polycaprolactone triol or diol. The photoinitiator may be comprised of n-phenyl glycine and di-camphorquinone. The unmatured polyesters may be blended with other biodegradable polyesters to optimize the physical properties of the composition, both before and after crosslinking.

Photoactivatable polymers are most preferred. Numerous photoactivatable molecules can be used in the production of photoactivatable polymers. However, the groups indicating the greatest level of utility are carbines and nitrenes formed photochemically from a precursor. Numerous methods of producing photoactivatable polymer are possible. With regard to the polymer, ideally the material should exhibit the following properties: a viscosity that allows it to flow through the lumen of the catheter; a photoactivatable functionality which allows it to crosslink intermolecularly as well as to the surrounding tissue; a crosslinked polymer should have sufficient structural integrity to withstand the systolic pressure present in the vasculature; the polymer should be biocompatible and the polymer should be capable of allowing tissue ingrowth to occur.

A synthetic or natural polymeric material specifically modified to contain chemical functionalities capable of being activated via light energy is most preferred. Examples of suitable substrate materials include collagen, fibrin as well as resorbable materials such as polylactic acid (PLA), polyglycolic acid (PGA), copolymers of PLA/PGA, polyphosphazenes, caprolactone, and polymers containing polyhydroxybutyric acid. Also non-resorbable polyphosphazenes, polyesters, polyurethanes, silicones and other non-resorbable polymers may be considered but are not preferred.

Numerous photoactivatable compounds exist to effect the crosslinking of the polymeric compound. One example of a photo-activatable molecule which may be used to initiate crosslinking of the polymer intermolecularly as well as to surrounding tissue is the aryl acid, sulfosuccinimidyl 6-(4'azido-2'-nitrophenylamino)hexanoate (Sulfo-SANPAH).

The synthetic or natural polymeric material may be specifically modified to also contain chemical functionalities capable of being chemically crosslinked. Examples of such a systems are polymers with primary amine terminating sidechains which may be crosslinked intermolecularly as well as with tissue using N-hydroxysuccinimide (NHS) ester crosslinkers such as BIS (Sulfosuccinimidyl) substrate. These materials may also be used for structural support or improving surface properties. A foamable TDI-based polyurethane pre-polymer may be used to foam and crosslink in situ upon mixing with water. The water solution may contain structural elements like collagen as well as agent like heparin.

The photo crosslinked as well as chemically crosslinked polymeric materials may be used as a drug delivery matrix with the incorporation of a desired drug. The drug delivery function may be the sole utility of the material or it may be used in combination with the other described functions.

The chemical and photo crosslinkers may have used to graft a molecule onto a substrate with the goal of binding a physiologically active molecule to it. An example of such a system would be grafting of polyethylemimine (PEI) to a surface followed by binding of heparin to it.

The photo or chemically crosslinkable material may be placed on the tissue contacting surface of an intraluminal graft or other implantable device and used to bond the device to tissue.

The following is a preferred example of a polymer which will meet various criteria of this invention.

EXAMPLE

A photoactivatable polymer may be produced utilizing polyphosphazine trimer as the starting material. Following extraction of impurities from the starting trimer via sublimation, polymerization of the polyphosphazene is effected by heating the material at 250° C. in a tube sealed under vacuum until such time that a substantial increase in viscosity is noted. The resulting polymer is further processed to remove the low molecular weight fractions via sublimation. The polymer thus created is dissolved in a suitable solvent such as anhydrous tetrahydrofuran for further reaction.

The polyphosphazene molecule is further prepared for attachment of the photoactivatable molecule by first stoichiometrically attaching an aliphatic molecule to the substrate in sufficient quantities to replace and convert the desired percentage of the available chlorine (Cl) groups of the polyphosphazene to non-reactable terminals thus leaving only a limited number of sites available for further reaction. One molecule that has been found to be particularly useful for the displacement of the Cl terminals is propylamine. The ultimate crosslink density will thus be determined (controlled) by limiting the number of available binding Cl sites on the substrate molecule. Once the appropriate quantity of Cl groups have been bound, the substrate is then ready for the attachment of the photoactivatable (BOC-propanolamine) molecule.

Continuous with the preparation process, a hydroxylamine compound is prepared in known manner for attachment to the previously prepared polyphosphazene by first creating the hyroxylamine group with a BOC-ON (N-terbutoxycarbonyl) groups thus protecting the amine terminal from further chemical modification. The BOC-ON protected molecule is subsequently attached to the polyphosphazene substrate via its hydroxy terminal.

Following attachment of the BOC-Hydroxylamine to the polyphosphazene, the BOC group is removed thus availing the primary amine group for use in the attachment of a photoactivatable compound such as SADP. Attachment of the photoactivable group is necessarily accomplished in the dark. The preparation process is known and is briefly described below:

The preparation of the photoactivated biopolymer is accomplished as follows: prepare polyphosphazine prepolymer (polymerize polyphosphazene); prepare hydroxylamine by attaching BOC group to amine terminal, stoichiometrically bind limited number of chlorine groups of the substrate molecule, attachment of BOC protected Hydroxylamine to substrate, remove BOC functionality to expose amine group, attach SADP group to the exposed primary amine terminal of the hydroxylamine.

What is claimed is as follows:

1. A multi-lumen stent forming catheter in combination with a source of polymeric stent forming material for the repair of vascular and the like anomalies, comprising:
   a) a source of polymeric stent forming material, said polymeric stent forming material being photo-curable, heat curable or chemically curable;
   b) said multi-lumen stent forming catheter having a proximal end and a distal end and consisting of:
      i) a main body of tubing having a proximal end portion and a distal end portion, and including at least three lumens, each of said at least three lumens having a proximal end and a distal end;
      ii) a percutaneous catheter balloon located at a distal end portion of the catheter, the balloon being unitary in construction and having a proximal end, a distal end and spaced end portions interconnected by an intermediate balloon portion of lesser diameter, said spaced end portions comprising first proximal enlarged and second enlarged distal balloon end portions when said balloon is at least partially inflated; the proximal balloon end portion of the balloon further comprises an outer surface, and first and second grooves extending over the surface to the space between the enlarged proximal and enlarged distal balloon end portions;
      iii) access means located at the proximal end portion of the tubing body, said access means providing access to the at least three lumens whereby a first lumen of said at least three lumens is used to inflate/deflate the balloon, a second lumen of said at least three lumens is a delivery lumen associated with the source of polymeric stent forming material and is used to deliver the polymeric material to the proximal enlarged end portion of the balloon, a third lumen of said at least three lumens is used as a vent lumen for flushing, drainage or removal of blood and biological material and/or venting to facilitate delivery of the polymeric stent forming material and one of said at least three lumens is used to insert into the balloon curing means for curing the polymeric stent forming material;
      iv) first small tubing means located at and associated with the proximal end portion of the balloon and in fluid communication with the delivery lumen and the access means, said first small tubing means being constructed and arranged so as to communicate between the delivery lumen and a region exterior of the balloon and located between the enlarged proximal and distal end portions of the balloon when at least partially inflated for the delivery of material therebetween; the first small tubing means is connected to the delivery lumen and fits in and extends along said first groove to the space between the first proximal and second distal enlarged balloon end portions of the balloon;
      v) second small tubing means located at and associated with the proximal end portion of the balloon and communicating with the vent lumen, said second small tubing means being constructed and arranged so as to communicate between the vent lumen and a region exterior of the balloon and located between the proximal and distal end portions of the balloon when said balloon is at least partially inflated for the delivery of the polymeric stent forming material therebetween, said second small tubing means thereby communicating between said region exterior of the balloon and the vent lumen for flushing, drainage or removal of blood and biological material and/or venting to facilitate delivery of the polymeric stent forming material, said balloon being constructed and arranged for use in shaping the polymeric stent forming material after introduction thereof and before curing thereof in situ; the second small tubing means is connected to the vent lumen and fits in and extends along said second groove to the space between the first proximal and second distal enlarged balloon end portions of the balloon; and
   c) curing means associated with and delivered by one of said at least three lumens for curing the polymeric stent forming material in situ.

* * * * *